United States Patent
Bao et al.

(10) Patent No.: US 11,946,923 B2
(45) Date of Patent: Apr. 2, 2024

(54) DEVICE AND METHOD FOR MONITORING FREEZING-THAWING DAMAGE OF UNDERWATER CONCRETE MEMBER IN SITU

(71) Applicant: QINGDAO UNIVERSITY OF TECHNOLOGY, Shandong (CN)

(72) Inventors: Jiuwen Bao, Qingdao (CN); Zihao Yu, Qingdao (CN); Peng Zhang, Qingdao (CN); Shuguo Li, Qingdao (CN); Tiejun Zhao, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 383 days.

(21) Appl. No.: 17/610,988

(22) PCT Filed: Feb. 4, 2021

(86) PCT No.: PCT/CN2021/075306
§ 371 (c)(1),
(2) Date: Nov. 12, 2021

(87) PCT Pub. No.: WO2022/041660
PCT Pub. Date: Mar. 3, 2022

(65) Prior Publication Data
US 2022/0308038 A1    Sep. 29, 2022

(30) Foreign Application Priority Data
Aug. 28, 2020    (CN) .......................... 202010884449.4

(51) Int. Cl.
*G01N 33/38* (2006.01)
*E02D 1/08* (2006.01)

(52) U.S. Cl.
CPC ............. *G01N 33/383* (2013.01); *E02D 1/08* (2013.01)

(58) Field of Classification Search
None
See application file for complete search history.

(56) References Cited

U.S. PATENT DOCUMENTS 8,215,172 B2 * 7/2012 Lootens ............... G01N 29/075
73/602

FOREIGN PATENT DOCUMENTS

| CN | 102353721 A | 2/2012 |
| CN | 102426196 A | 4/2012 |

(Continued)

OTHER PUBLICATIONS

Jun. 4, 2021 International Search Report issued in International Patent Application No. PCT/CN2021/075306.

(Continued)

*Primary Examiner* — Peter J Macchiarolo
*Assistant Examiner* — Jermaine L Jenkins
(74) *Attorney, Agent, or Firm* — Oliff PLC

(57) ABSTRACT

A device and method for monitoring freezing-thawing damage of an underwater concrete member in situ. A main structure includes an upper link, concrete member, transverse sealed box, longitudinal sealed box, movable guide rod, probe launching box, multichannel data collector, frequency modulation transmitter, computer, auxiliary wheels, lower link, and a wireless temperature sensor. A process includes four steps: launching of a probe, collection of data, calculation of an elastic modulus, and evaluation of freezing-thawing damage. The device is simply structured, easy to operate, and can be reused, and provides power for launching the probe by non-contact force transmission by using high-strength magnets of the same pole, resolving the sealing problem, and calculates the elastic modulus of the concrete member by using acceleration data obtained by a probe, so as to obtain a loss amount of the elastic modulus, (Continued)

thereby performing real-time in-situ monitoring for freezing-thawing damage of an underwater concrete member.

6 Claims, 2 Drawing Sheets

(56) References Cited

FOREIGN PATENT DOCUMENTS

| | | | | | |
|---|---|---|---|---|---|
| CN | 104345093 | A | | 2/2015 | |
| CN | 107044933 | A | | 8/2017 | |
| CN | 108152158 | A | | 6/2018 | |
| CN | 108254247 | A | * | 7/2018 | ............. G01B 21/32 |
| CN | 108459083 | A | | 8/2018 | |
| CN | 109632971 | A | | 4/2019 | |
| CN | 110160870 | A | * | 8/2019 | |
| CN | 110730516 | A | | 1/2020 | |
| CN | 111965338 | A | | 11/2020 | |
| CN | 212255335 | U | | 12/2020 | |
| IN | 102141542 | A | | 8/2011 | |
| JP | H11-133009 | A | | 5/1999 | |
| JP | 2011-043427 | A | | 3/2011 | |

OTHER PUBLICATIONS

Jun. 4, 2021 Written Opinion of the International Searching Authority issued in International Patent Application No. PCT/CN2021/075306.

* cited by examiner

DEVICE AND METHOD FOR MONITORING FREEZING-THAWING DAMAGE OF UNDERWATER CONCRETE MEMBER IN SITU

TECHNICAL FIELD

The present invention belongs to the technical field of monitoring of durability of concrete structures, and relates to a device and method for monitoring freezing-thawing damage of an underwater concrete member in situ, which performs assessment for the freezing-thawing damage of the underwater concrete member in situ by motoring an elastic modulus of the underwater concrete member.

BACKGROUND

In a cold region or a freezing-thawing environment, since moisture in gaps inside a concrete member generates a frozen-heave stress as a result of freezing, different degrees of damage is caused to the concrete member, adversely affecting safety and durability. A device and method for on-site measurement of an elastic modulus of a concrete member are mainly applicable to concrete members on land. For example, the Chinese patent 201710222638.3 discloses a level-equipped device for measuring an elastic modulus of concrete, which includes an upper ring and a lower ring. The upper ring and the lower ring are respectively arranged in an upper position and a lower position, and are both provided with a fastening device for fixing to-be-measured concrete. The upper ring is further provided with a circular level. A positioning plate is fixed between the upper ring and the lower ring. The positioning plate is configured to fix a distance between the upper ring and the lower ring. A dial indicator support is disposed on the upper ring, and a contact rod is disposed on the lower ring. A dial indicator is placed between the dial indicator support and the contact rod, which calculates an elastic modulus value of the concrete by using a slight deformation between fixing frames. The Chinese patent 201810780463.2 discloses a portable dynamic elastic modulus measurer controlled by a mobile terminal, which includes a host, a transmitter, and a receiver. The host includes a broadcast module, a device connection module, a processor, and a lithium ion battery, which is a cuboid. The broadcast module, the device connection module, the processor, and the lithium ion battery are mounted inside the host. The transmitter and the receiver are outside the host. The transmitter and the receiver are connected to the host by using a cable. The mobile terminal and the device connection module of the device come into a one-to-one connection and perform bidirectional wireless communication by using the broadcast module. The device connection module is configured to transmit identification information of the device to a target mobile terminal before broadcasting of the broadcast module, so that the mobile terminal can accurately and quickly control the device. The broadcast module is configured to transmit information between the mobile terminal and the device. The processor is configured to control turn-on/off and adjustment of the transmitter and the receiver, convert information received by the broadcast module to a digital signal, and transmit the signal to the transmitter. The receiver is configured to transmit a detected signal to the processor. The processor is configured to convert the signal and transmit the signal to the mobile terminal by using the broadcast module. The mobile terminal is configured to control the device, calculate data, and display a result. The expression "calculate data and display a result" means that the mobile terminal performs a series of calculations such as Fourier transform on the received data by using the processor thereof to obtain a resonance frequency, displays a real-time occurring frequency, and a spectrogram and a current amplitude frequency at a current frequency, and automatically displays a dynamic elastic modulus calculated by using the resonance frequency upon completion of scanning. The mobile terminal may download a social client or an offline app to control the device. The mobile terminal measures a frequency and an amplitude of a to-be-measured member and performs a series of calculations such as Fourier transform to obtain a resonance frequency, and calculates a dynamic elastic modulus by using the resonance frequency. The Chinese patent 201810188114.1 discloses a method for measuring an elastic modulus of concrete based on surface-attached PZT. The method includes the following steps: Step S1: Transmit a preset excitation signal to a PZT exciter attached to a surface of to-be-measured concrete. Step S2: Receive, by using a PZT sensor array, a velocity measurement signal generated by the PZT exciter, and obtain a Rayleigh wave velocity CR according to the received velocity measurement signal, where the velocity measurement signal is a stress wave generated by the PZT exciter under excitation of the preset excitation signal. Step S3: Obtain an elastic modulus E of the concrete by using the Rayleigh wave velocity CR. The Rayleigh wave velocity is measured by using the PZT exciter and the PZT sensor array attached to the surface of the concrete, and the elastic modulus of the concrete is obtained according to the Rayleigh wave velocity. However, an underwater concrete member is exposed to a low-temperature and high-pressure environment for a long period of time, which is more prone to freezing-thawing damage compared with concrete members on land. Moreover, a special underwater environment results in a function failure of a current elastic modulus measurement device. Therefore, currently, in order to measure a mechanical property of the underwater concrete member, usually, a diver takes a core underwater, and an elastic modulus is obtained on land. Not only a life threat is brought to underwater workers, but also an obtained elastic modulus measurement result is limited by factors such as season, temperature, time, economic condition, and the like, which is not continuous and representative. As a result, a degree of the freezing-thawing damage of the concrete member cannot be precisely evaluated. Therefore, performing in-situ elastic modulus measurement on a built underwater concrete member to evaluate a degree of freezing-thawing damage thereof is of great significance.

SUMMARY

The present invention is intended to overcome the shortcomings of the prior art such as a failure of continuously monitoring freezing-thawing damage of an underwater concrete member in situ in real-time, and seeks to design a device and method for monitoring freezing-thawing damage of an underwater concrete member in situ based on an elastic modulus.

In order to achieve the foregoing objective, a main structure of the device for monitoring freezing-thawing damage of an underwater concrete member involved in the present invention includes an upper link, a concrete member, a transverse sealed box, a longitudinal sealed box, a movable guide rod, a probe launching box, a multichannel data collector, a frequency modulation transmitter, a computer, auxiliary wheels, a lower link, and a wireless temperature sensor. One end of the upper link is connected to the concrete member, and an other end of the upper link is connected to the transverse sealed box. The transverse sealed box is connected to the longitudinal sealed box and the movable guide rod. The longitudinal sealed box is connected to the probe launching box by using a secondary pulley disposed in the longitudinal sealed box. The probe launching box is connected to the multichannel data collector. The multichannel data collector is connected to the computer by using the frequency modulation transmitter. The movable guide rod extends through two columns of auxiliary wheels disposed on the probe launching box to be connected to one end of the lower link. an other end of the lower link is connected to the concrete member. The wireless temperature sensor is disposed on the lower link. The computer is connected to the transverse sealed box, the probe launching box, and the wireless temperature sensor, and the computer stores an equation for calculating an elastic modulus of the concrete member.

A waterproof power supply #1 and a submersible motor are disposed in the transverse sealed box, the waterproof power supply #1 is connected to the submersible motor by using a wireless switch #1, and a primary pulley, a reel, and a guide wheel are disposed on the submersible motor.

A transmission chain involved in the present invention is connected to the primary pulley, the reel, and the secondary pulley in sequence by using the guide wheel.

A waterproof power supply #2 and a spring set are disposed inside the probe launching box. The waterproof power supply #2 is connected to an electromagnet by using a wireless switch #2. The spring set is connected to a steel plate bracket. An iron block is disposed on a left end of the steel plate bracket. A magnet #1 is disposed on a right end of the steel plate bracket. A hollow conduit is disposed on an end portion of the probe launching box. A magnet #2 is disposed on an inner end of the conduit. A pulley is disposed on an outer end of the conduit. A launching guide rod is disposed in the conduit. A rubber seal ring is disposed between the conduit and the launching guide rod. A probe is disposed on an end portion of the launching guide rod.

The upper link involved in the present invention is connected to the concrete member and the transverse sealed box. The lower link is connected to the concrete member and the movable guide rod. The probe launching box is connected to the auxiliary wheels, by using a locking nut. Sealing is performed among the transverse sealed box, the probe launching box, and the locking nut and between the probe launching box and the secondary pulley, so that a desirable waterproof effect is achieved. The transverse sealed box, the longitudinal sealed box, and the probe launching box are electrical sealed boxes made of stainless steel having a thickness of 5 mm. The upper link and the lower link are seamless steel pipes having an outer diameter of 15 mm and an inner diameter of 8 mm, to ensure that the upper link and the lower link are evenly stressed and respective weights can be reduced. The multichannel data collector is electrically connected to the probe. The frequency modulation transmitter is a bidirectional frequency modulation transmitter. The waterproof power supply #1 and the waterproof power supply #2 are both lithium batteries. The wireless temperature sensor is capable of monitoring a water temperature in real time to indicate whether the concrete member is in a freezing-thawing status. The submersible motor is an oil-filled submersible motor. The magnet #1 and the magnet #2 are both N-pole strong magnets. The probe is an acceleration probe.

The computer involved in the present invention stores an equation $$E_2 = \frac{39.3mE_1(1-\mu_2)^2}{16(Rv_c)^{0.5}\tau^{2.5}E_1 - 39.3m(1-\mu_1)^2}$$

for calculating the elastic modulus of the concrete member. $E_2$ is the elastic modulus of the concrete member in MPa, m is mass of the probe in kg, $E_1$ is an elastic modulus of a probe in MPa, $\mu_2$ is a Poisson's ratio of the concrete member having a dimension of 1, R is an equivalent radius of the probe in m, $v_c$ is a speed at which the probe impacts the concrete member in m/s, $\tau$ is an impact duration of the probe in s, $\mu_1$ is a Poisson's ratio of the probe having a dimension of 1, and the equivalent radius R, the Poisson's ratio $\mu_1$, the elastic modulus $E_1$, and the mass m of the probe are known.

A process of a method for monitoring freezing-thawing damage of an underwater concrete member in situ involved in the present invention includes the following four steps:

I, launching of a probe including: uploading, by a wireless temperature sensor when detecting a water temperature higher than 0° C. near a concrete member, the water temperature to a computer, turning on, by the computer, a wireless switch #2, so that an electromagnet is energized and generates magnetism, an iron block is attracted to the electromagnet, a steel plate bracket is moved leftward, and a spring set is compressed, and turning off, by the computer, the wireless switch #2, so that the electromagnet is demagnetized, the iron block is released, the spring set is restored to an original shape while driving the steel plate bracket to move rightward, and a repulsive force is generated between a magnet #1 and a magnet #2 and pushes a launching guide rod out, so that a probe impacts the concrete member;

II, collection of data including: acquiring, after the probe impacts the concrete member, data such as a speed at which the probe impacts the concrete member and a duration of the impact, transmitting the data to a multichannel data collector and then to the computer by using a frequency modulation transmitter, turning on, by the computer, a wireless switch #1, so that a submersible motor drives a primary pulley to rotate, a reel collects a transmission chain transmitted by the primary pulley, and the transmission chain drives a probe launching box to move upward by using a secondary pulley, repeating step I such that the probe impacts different positions of the concrete member, and transmitting data acquired by the probe to the computer, where when the reel releases the transmission chain, the secondary pulley drives the probe launching box to move downward, and a movable guide rod is moved between two columns of auxiliary wheels during the upward and downward movement of the probe launching box, to guide and stably maintain the upward and downward movement of the probe launching box;

III, calculation of an elastic modulus including: calculating, by the computer, an elastic modulus of the concrete member in real time according to the data transmitted by the frequency modulation transmitter and an elastic modulus calculation equation, drawing a variation curve of the elastic modulus of the concrete member in real time by using Matrix laboratory (Matlab) and Origin (a function drawing software), and analyzing a law of the elastic modulus varying with time; and IV, evaluation of freezing-thawing damage including: evaluating the freezing-thawing damage of the concrete member according to the elastic modulus of the concrete member, the variation curve of the elastic modulus, and the law of the elastic modulus varying with time that are obtained in step III, and determining that the concrete member has been subjected to freezing-thawing damage when a loss rate of the elastic modulus reaches 60%.

Compared with the prior art, in the present invention, the probe transmits the measured acceleration data to the multichannel data collector and then to the computer in real time by using the frequency modulation signal transmitter. The computer obtains the elastic modulus of the concrete member by using the calculation equation according to a relationship between an acceleration and time during the impact of the probe on the concrete member, and draws a variation curve of the elastic modulus of the concrete member in real time. The probe capable of moving upward and downward helps monitor elastic moduli of different portions of the concrete member. In this way, simple, fast, accurate, and continuous measurement of the elastic modulus of the underwater concrete member is realized. The present invention is simply structured and easy to operate, and can be reused. The present invention provides power for the launching of the probe by means of non-contact force transmission by using high-strength magnets of the same pole, resolving the sealing problem, and calculates the elastic modulus of the concrete member by using acceleration data obtained by a probe, so as to obtain a loss amount of the elastic modulus, thereby performing real-time in-situ monitoring for the freezing-thawing damage of the underwater concrete member. The present invention resolves problems such as a high cost, a high risk factor, data discontinuation, and the like of the real-time monitoring of the freezing-thawing damage of the underwater concrete member, and avoids human reading errors.

DETAILED DESCRIPTION

Figure 1:
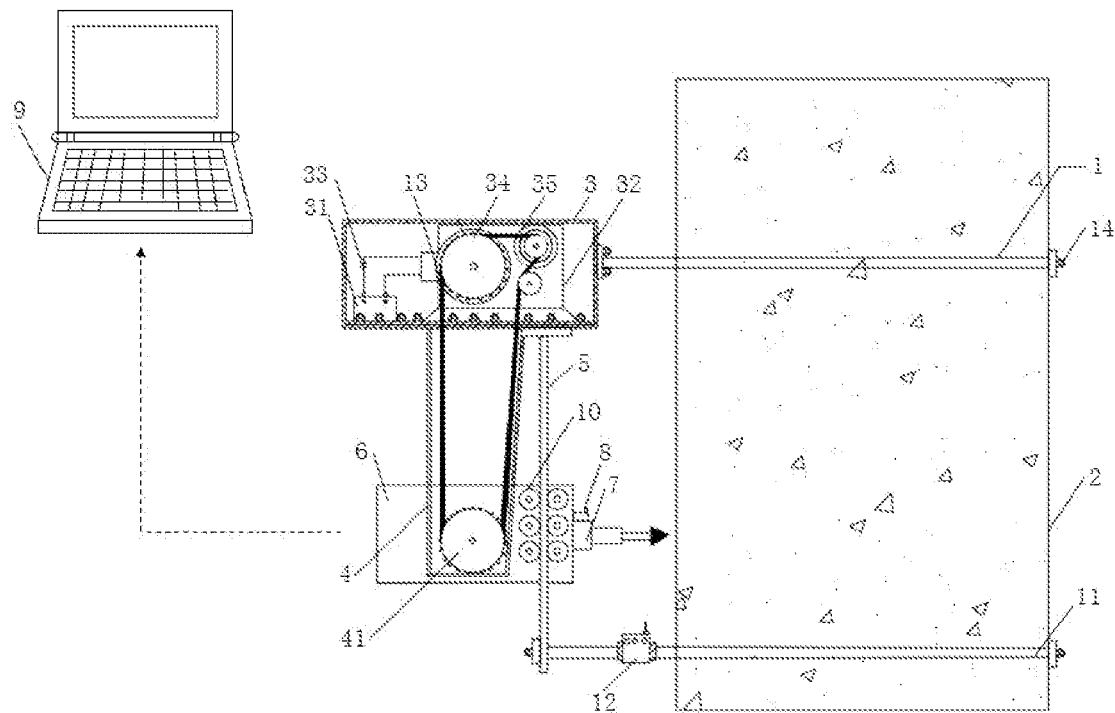
FIG. 1 is a schematic principle diagram of a main structure according to the present invention.
Figure 2:
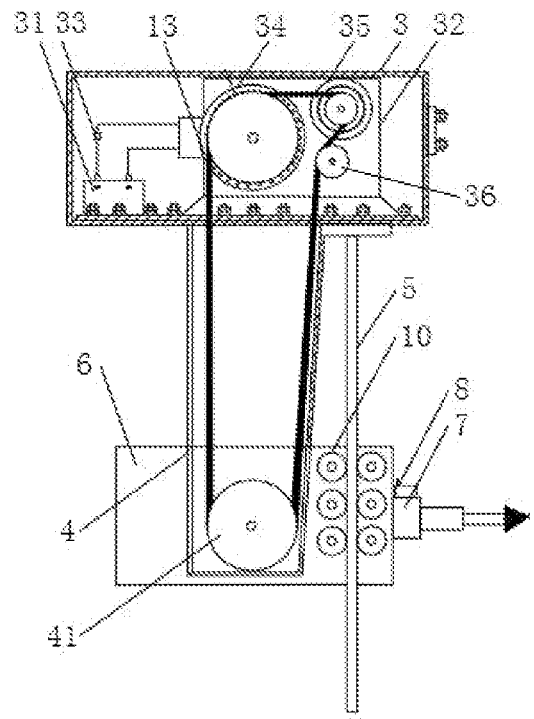
FIG. 2 is a schematic principle diagram of a partial structure according to the present invention.
Figure 3:
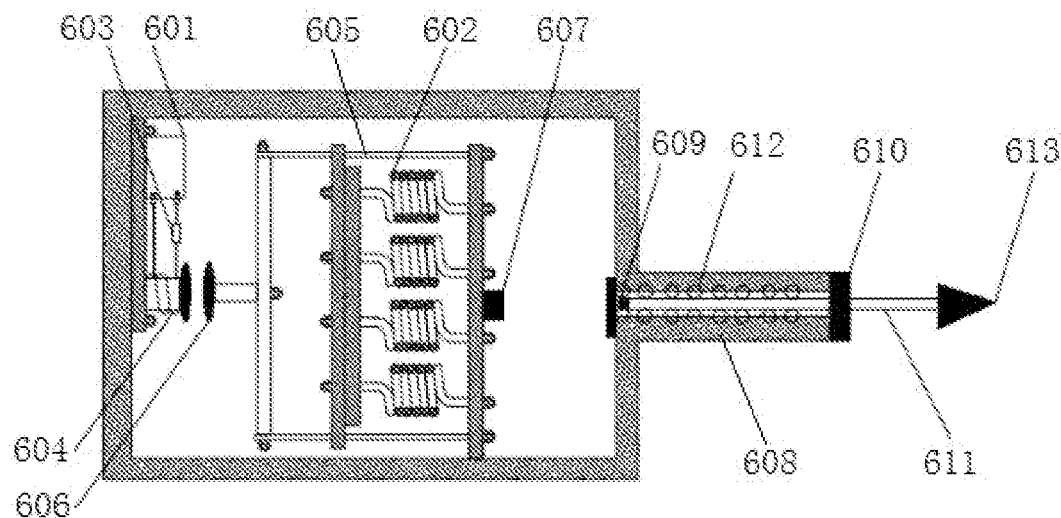
FIG. 3 is a schematic principle diagram of an internal structure of a probe launching box according to the present invention.
Figure 4:
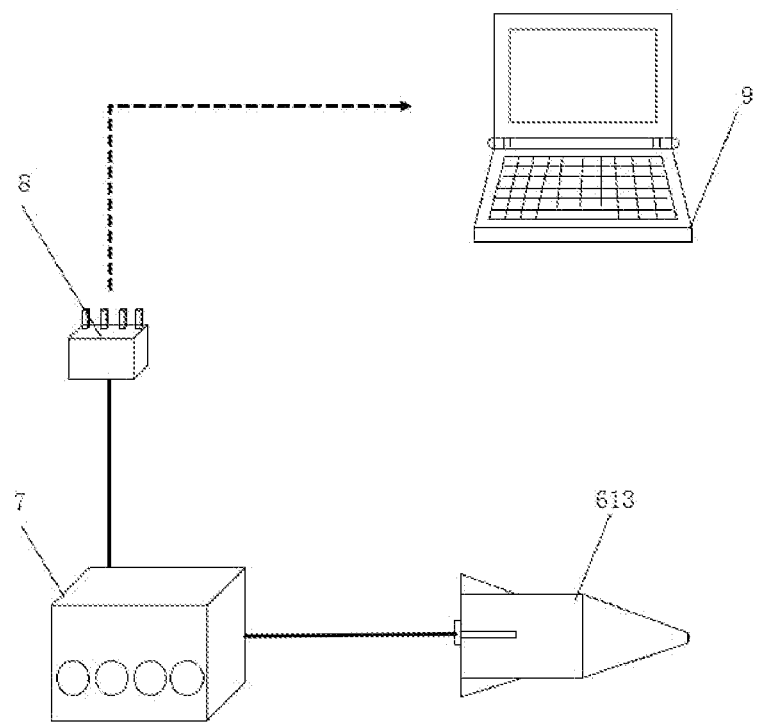
FIG. 4 is a schematic principle diagram of data transmission according to the present invention.

The present invention is further described below by using the embodiments and the accompanying drawings.

Embodiment 1

A main structure of a device for monitoring freezing-thawing damage of an underwater concrete member involved in this embodiment includes an upper link 1, a concrete member 2, a transverse sealed box 3, a longitudinal sealed box 4, a movable guide rod 5, a probe launching box 6, a multichannel data collector 7, a frequency modulation transmitter 8, a computer 9, auxiliary wheels 10, a lower link 11, a wireless temperature sensor 12, a transmission chain 13, a locking nut 14, a waterproof power supply #1 31, a submersible motor 32, a wireless switch #1 33, a primary pulley 34, a reel 35, a guide wheel 36, a secondary pulley 41, a waterproof power supply #2 601, a spring set 602, a wireless switch #2 603, an electromagnet 604, a steel plate bracket 605, an iron block 606, a magnet #1 607, a conduit 608, a magnet #2 609, a pulley 610, a launching guide rod 611, a rubber seal ring 612, and a probe 613. One end of the upper link 1 of having a hollow tubular structure is connected to the concrete member 2 of an underwater structure, and an other end of the upper link is connected to the transverse sealed box 3 having a cuboid structure. The transverse sealed box 3 is connected to the longitudinal sealed box 4 having a cuboid structure and the movable guide rod 5 having a hollow structure. The waterproof power supply #1 31 and the submersible motor 32 are disposed inside the transverse sealed box 3. The waterproof power supply #1 31 and the submersible motor 32 are connected by using the wireless switch #1 33. The primary pulley 34 having a circular structure, the reel 35, and the guide wheel 36 are disposed on the submersible motor 32. The secondary pulley 41 having a circular structure is disposed inside the longitudinal sealed box 4. The transmission chain 13 is connected to the primary pulley 34, the reel 35, and the secondary pulley 41 by using the guide wheel 36 in turn to form a closed loop. The longitudinal sealed box 4 is connected to the probe launching box 6 having a cuboid structure. The waterproof power supply #2 601 and the spring set 602 including four springs are disposed inside the probe launching box 6. The waterproof power supply #2 601 is connected to the electromagnet 604 by using the wireless switch #2 603. The spring set 602 is disposed around interior of the steel plate bracket 605. The iron block 606 is disposed on a left end of the steel plate bracket 605, and the magnet #2 607 is disposed on a right end of the steel plate bracket 605. The conduit 608 having a hollow structure is disposed on an end portion of the probe launching box 6. The magnet #2 609 is disposed on an inner end of the conduit 608, and the pulley 610 is disposed on an outer end of the conduit 608. The launching guide rod 611 is disposed in the conduit 608. The rubber seal ring 612 is disposed between the conduit 608 and the launching guide rod 611. The probe 613 is disposed on an end portion of the launching guide rod 611. The probe launching box 6 is connected to the multichannel data collector 7. The multichannel data collector 7 is connected to the computer 9 by using the frequency modulation transmitter 8. The movable guide rod 5 extends through two columns of auxiliary wheels 10 disposed on the probe launching box 6 to be connected to one end of the lower link 11. An other end of the lower link 11 is connected to the concrete member 2. The wireless temperature sensor 12 is disposed on the lower link 11. The computer 9 is connected to the transverse sealed box 3, the probe launching box 6, and the wireless temperature sensor 12. The upper link 1 is connected to the concrete member 2 and the transverse sealed box 3, the lower link 11 is connected to the concrete member 2 and the movable guide rod 5, and the probe launching box 6 is connected to the auxiliary wheels 10, by using the locking nut 14. The multichannel data collector 7 is electrically connected to the probe 613.

During use of the device for monitoring freezing-thawing damage of an underwater concrete member in situ involved in this embodiment, upon energization of the electromagnet 604, the iron block 606 is attracted, and the steel plate bracket 605 compresses the spring set 602. Upon deenergization of the electromagnet 604, a magnetic force disappears, and the spring set 602 is restored to an original status while driving the steel plate bracket 605 to move rightward quickly, so that the magnet #1 607 and the magnet #2 609 repel each other. The repulsive force launches the probe 613 to the concrete member 2 by using the launching guide rod 611, to generate an impact.

The upper link 1 and the lower link 11 involved in this embodiment are both non-destructively connected to the concrete member 2, to ensure integrity of the concrete member 2. The primary pulley 34 on the submersible motor 32 is connected to the secondary pulley 41 on the probe launching box 6, and the movable guide rod 5 is in contact with the auxiliary wheels 10 on the probe launching box 6, so that the probe 613 can move upward and downward stably. The probe 613 is connected to the multichannel data collector 7, the multichannel data collector 7 is connected to the frequency modulation transmitter 8, and the frequency modulation transmitter 8 is connected to the computer 9, so that data acquired by the probe 613 can be quickly transmitted to the computer 9.

Embodiment 2

The method for monitoring freezing-thawing damage of an underwater concrete member in situ involved in this embodiment is used to monitor an underwater concrete member 2. When a wireless temperature sensor 12 displays an underwater temperature higher than 0° C., the water temperature is uploaded to the computer 9. The computer 9 turns on the wireless switch #1 33, The submersible motor 32 drives the primary pulley 34 to rotate. The reel 35 collects the transmission chain 13 transmitted by the primary pulley 34. The transmission chain 13 drives the probe launching box 6 to move upward by using the secondary pulley 41, so that the probe 613 is located above the concrete member 2. In addition, the computer 9 turns on the wireless switch #2 603, so that the electromagnet 604 is energized and generates magnetism, the iron block 606 is attracted to the electromagnet 604, the steel plate bracket 605 is moved leftward, and the spring set 602 is compressed. The computer 9 turns off the wireless switch #2 603, so that the electromagnet 604 is demagnetized, the iron block 606 is released, the spring set 602 is restored to an original shape while driving the steel plate bracket 605 to move rightward, and a repulsive force is generated between the magnet #1 607 and the magnet #2 609 and pushes the launching guide rod 611 out, so that the probe 603 impacts the concrete member 2. The monitoring is performed on the concrete member 2 every 20 cm. The multi-channel data collector 7 transmits collected data such as a speed at which the probe 613 impacts the concrete member 2 and an impact duration to the computer 9 by using a signal by means of the frequency modulation transmitter 8. The computer 9 draws a variation curve of the elastic modulus of the concrete member 2 in real time by using a matrix laboratory (Matlab) and Origin (function drawing software), analyzes a law of the elastic modulus varying with time, and determines whether the concrete member 2 has been subjected to freezing-thawing damage according to whether when a loss rate of the elastic modulus reaches 60%.

What is claimed is:

1. A device for monitoring freezing-thawing damage of an underwater concrete member in situ, wherein a main structure comprises an upper link, a concrete member, a transverse sealed box, a longitudinal sealed box, a movable guide rod, a probe launching box, a multichannel data collector, a frequency modulation transmitter, a computer, auxiliary wheels, a lower link, and a wireless temperature sensor, wherein one end of the upper link is connected to the concrete member, an other end of the upper link is connected to the transverse sealed box, the transverse sealed box is connected to the longitudinal sealed box and the movable guide rod, the longitudinal sealed box is connected to the probe launching box by using a secondary pulley disposed in the longitudinal sealed box, the probe launching box is connected to the multichannel data collector, the multichannel data collector is connected to the computer by using the frequency modulation transmitter, the movable guide rod extends through two columns of auxiliary wheels disposed on the probe launching box to be connected to one end of the lower link, an other end of the lower link is connected to the concrete member, the wireless temperature sensor is disposed on the lower link, the computer is connected to the transverse sealed box, the probe launching box, and the wireless temperature sensor, and the computer stores an equation for calculating an elastic modulus of the concrete member:

$$E_2 = \frac{39.3mE_1(1-\mu_2)^2}{16(Rv_c)^{0.5}\tau^{2.5}E_1 - 39.3m(1-\mu_1)^2},$$

wherein $E_2$ is the elastic modulus of the concrete member in MPa, m is mass of the probe in kg, $E_1$ is an elastic modulus of a probe in MPa, $\mu_2$ is a Poisson's ratio of the concrete member having a dimension of 1, R is an equivalent radius of the probe in m, $v_c$ is a speed at which the probe impacts the concrete member in m/s, $\tau$ is an impact duration of the probe in s, $\mu_1$ is a Poisson's ratio of the probe having a dimension of 1, and the equivalent radius R, the Poisson's ratio $\mu_1$, the elastic modulus $E_1$, and the mass m of the probe are known.

2. The device for monitoring freezing-thawing damage of an underwater concrete member in situ according to claim 1, wherein a waterproof power supply #1 and a submersible motor are disposed in the transverse sealed box, the waterproof power supply #1 is connected to the submersible motor by using a wireless switch #1, and a primary pulley, a reel, and a guide wheel are disposed on the submersible motor.

3. The device for monitoring freezing-thawing damage of an underwater concrete member in situ according to claim 2, wherein a transmission chain is connected to the primary pulley, the reel, and the secondary pulley in sequence by using the guide wheel.

4. The device for monitoring freezing-thawing damage of an underwater concrete member in situ according to claim 3, wherein a waterproof power supply #2 and a spring set are disposed inside the probe launching box, the waterproof power supply #2 is connected to an electromagnet by using a wireless switch #2, the spring set is connected to a steel plate bracket, an iron block is disposed on a left end of the steel plate bracket, a magnet #1 is disposed on a right end of the steel plate bracket, a hollow conduit is disposed on an end portion of the probe launching box, a magnet #2 is disposed on an inner end of the conduit, a pulley is disposed on an outer end of the conduit, a launching guide rod is disposed in the conduit, a rubber seal ring is disposed between the conduit and the launching guide rod, and a probe is disposed on an end portion of the launching guide rod.

5. The device for monitoring freezing-thawing damage of an underwater concrete member in situ according to claim 4, wherein the upper link is connected to the concrete member and the transverse sealed box, the lower link is connected to the concrete member and the movable guide rod, and the probe launching box is connected to the auxiliary wheels, by using a locking nut, sealing is performed among the transverse sealed box, the probe launching box, and the locking nut and between the probe launching box and the secondary pulley, the transverse sealed box, the longitudinal sealed box, and the probe launching box are electrical sealed boxes made of stainless steel having a thickness of 5 mm, the upper link and the lower link are seamless steel pipes having an outer diameter of 15 mm and an inner diameter of 8 mm, the multichannel data collector is electrically connected to the probe, the frequency modulation transmitter is a bidirectional frequency modulation transmitter, the waterproof power supply #1 and the waterproof power supply #2 are both lithium batteries, the wireless temperature sensor is capable of monitoring a water temperature in real time to indicate whether the concrete member is in a freezing-thawing status, the submersible motor is an oil-filled submersible motor, the magnet #1 and the magnet #2 are both N-pole strong magnets, and the probe is an acceleration probe.

6. A method for monitoring freezing-thawing damage of an underwater concrete member in situ, wherein a process comprises:
- I, launching of a probe comprising: when a wireless temperature sensor detects a water temperature higher than 0° C. near a concrete member, uploading the water temperature to a computer, turning on, by the computer, a wireless switch #2, so that an electromagnet is energized and generates magnetism, an iron block is attracted to the electromagnet, a steel plate bracket is moved leftward, and a spring set is compressed, and turning off, by the computer, the wireless switch #2, so that the electromagnet is demagnetized, the iron block is released, the spring set is restored to an original shape while driving the steel plate bracket to move rightward, and a repulsive force is generated between a magnet #1 and a magnet #2 and pushes a launching guide rod out, so that a probe impacts the concrete member;
- II collection of data comprising: acquiring, after the probe impacts the concrete member, data such as a speed at which the probe impacts the concrete member and a duration of the impact, transmitting the data to a multichannel data collector and then to the computer by using a frequency modulation transmitter, turning on, by the computer, a wireless switch #1, so that a submersible motor drives a primary pulley to rotate, a reel collects a transmission chain transmitted by the primary pulley, and the transmission chain drives a probe launching box to move upward by using a secondary pulley, repeating step I such that the probe impacts different positions of the concrete member, and transmitting data acquired by the probe to the computer, wherein
when the reel releases the transmission chain, the secondary pulley drives the probe launching box to move downward, and a movable guide rod is moved between two columns of auxiliary wheels during the upward and downward movement of the probe launching box, to guide and stably maintain the upward and downward movement of the probe launching box;
- III, calculation of an elastic modulus comprising: calculating, by the computer, an elastic modulus of the concrete member in real time according to the data transmitted by the frequency modulation transmitter and an elastic modulus calculation equation, drawing a variation curve of the elastic modulus of the concrete member in real time by using Matlab and Origin, and analyzing a law of the elastic modulus varying with time; and
- IV, evaluation of freezing-thawing damage comprising: evaluating the freezing-thawing damage of the concrete member according to the elastic modulus of the concrete member, the variation curve of the elastic modulus, and the law of the elastic modulus varying with time that are obtained in step III, and determining that the concrete member has been subjected to freezing-thawing damage when a loss rate of the elastic modulus reaches 60%.

* * * * *